(12) United States Patent
Tillet

(10) Patent No.: US 6,548,554 B1
(45) Date of Patent: Apr. 15, 2003

(54) IONIC AQUEOUS COMPOSITION CONTAINING LEVOMENTHOL

(75) Inventor: Yves Théodore Tillet, Chelles (FR)

(73) Assignee: P. N. Gerolymatos S.A., Kryoneri Athens (GR)

( * ) Notice: Subject to any disclaimer, the term of this patent is extended or adjusted under 35 U.S.C. 154(b) by 0 days.

(21) Appl. No.: 09/646,919

(22) PCT Filed: Apr. 13, 1999

(86) PCT No.: PCT/FR99/00860
§ 371 (c)(1),
(2), (4) Date: Oct. 13, 2000

(87) PCT Pub. No.: WO99/52520
PCT Pub. Date: Oct. 21, 1999

(30) Foreign Application Priority Data

Apr. 14, 1998 (FR) .............................. 98 04809

(51) Int. Cl.$^7$ ...................... A61K 31/045; A61K 31/05; A61F 13/00; A61F 9/02
(52) U.S. Cl. ........................ 514/729; 514/731; 424/434; 424/437
(58) Field of Search ................................ 514/731, 730, 514/724, 829, 385, 729; 424/434, 437

(56) References Cited

PUBLICATIONS

"The effect of L–menthol stimulation of the major palatine nerve on subjective and objective nasal patency", Naito et al., Auris Nasus Larynx, (1997): Abstract.*
"Rhinospray Plus", Drug Launches, (Mar. 20, 1995).*
Ocean nasal spray brochure, Fleming and company, 1975.*
Nishino et al., "Nasal Inhalation of I–methol reduces respiratory discomfort associated with loaded breathing", Am. J. Respir. Crit. Care Med., vol. 156, No. 1, 1997, 309–313.*

* cited by examiner

*Primary Examiner*—Zohreh Fay
*Assistant Examiner*—Brian-Yong S. Kwon

(57) ABSTRACT

A composition for relieving a sensation of respiratory discomfort and/or for promoting natural regeneration of mucous membranes of the nasal cavity. The composition contains levomenthol at a concentration between 10 and 250 mg/l, dissolved in an aqueous ionic solution having an osmolarity at least equal to that of an aqueous solution of sodium chloride at 9 g/l. The aqueous ionic solution is pure sea water, diluted sea water, an aqueous sodium chloride solution, an aqueous sodium chloride solution further containing at least one salt found in sea water, or a mixture thereof.

26 Claims, No Drawings

IONIC AQUEOUS COMPOSITION CONTAINING LEVOMENTHOL

BACKGROUND OF THE INVENTION

This application is a filing under 35 USC 371 of PCT/FR99/00860 filed Apr. 13, 1999.

The present invention relates to an ionic aqueous composition containing levomenthol.

The nasal cavity contains sensitive receptors which are stimulated by the passage of air. When external modifications intervene, such as infestation by rhinovirus, variations in temperature or in atmospheric pressure for example, the mucous membranes of the nasal cavity react and get congested, and this creates a feeling of a blocked nose. This benign affectation, which is commonly called the cold, normally gets better spontaneously but sometimes does lead, over several days, to a sensation of respiratory discomfort and a secretory malfunctioning of the nasal mucous membranes, which can give rise to a significant discomfort under numerous circumstances such as at work or for sleeping suitably, for example.

Several treatments are currently proposed. Via the general route or via the local route, these are medicaments which have a vasoconstrictory action. Their long term use can however cause local or general side-effects which are linked to their pharmacological action, which can be serious, such as an atrophy of the nasal mucous membranes or cardio-vascular or prostate troubles. Another treatment consists in the local administration of essential oils and/or of terpenic aromatic derivatives. Their local decongestant or antiseptic action, often claimed, is not however scientifically proved, and their use, alone or in combination, can prove to be dangerous for health by risking causing local irritations with the essential oils, or central nervous system troubles, such as convulsions in the infant with camphor, for example. The risk is increased when these preparations contain alcohol, even in low proportions, or antiseptic substances, used for preventing microbial contamination but which can be irritants to the nasal mucous membranes. Infants, young children or elderly subjects are more particularly exposed to all these risks.

Natural menthol is a secondary alcohol of essence of mint which contains levomenthol but also menthone. Synthetic menthol or dl menthol is an alcohol which is obtained by various synthetic methods, but 1-menthol or levomenthol, which is the most active isomer for aromatisation, can also be isolated or synthesised (cf. Codex 1965-DORVAULT L'OFFICINE, Vigot, 23$^{rd}$ ed. p.1055-MARTINDALE, THE EXTRA PHAMARCOPEIA, The Pharmaceutical Press, 30$^{th}$ ed. p. 1386).

It has already been proposed to use menthol, even levomenthol in compositions which are intended for decongesting the nasal mucous membranes.

However, menthol being known for its low solubility in aqueous solution, various tricks are used for using it at concentrations higher than its limit of solubility in water, either by incorporating it in emulsions, or by introducing various organic products such as an oil or an alcohol to improve its dispersion.

SUMMARY OF THE INVENTION

The present invention results from a reverse process since the inventor has now discovered that it was possible to prepare particularly effective compositions by using levomenthol at a concentration which does not go over the limit of solubility of this latter compound, with the proviso of dissolving it in a sufficiently ionic aqueous medium, and more specifically a medium which is at least isotonic, and preferably even quite clearly hypertonic.

It will be recalled that in physiology, the term <<isotonic>> is qualified as as solution which exerts an osmotic pressure which is equal to that of normal blood plasma, e.g. physiological NaCl solute at 9 g per liter. A hypertonic solution means a solution which exerts an osmotic pressure which is greater than that of normal bold plasma (example: NaCl solute the concentration of which is greater than 9 g per liter). It is in this sense that it is necessary to understand the terms <<isotonic>> or <<hypertonic>>.

As it emerges from the following description, insofar as solutions are covered here which optionally contain ions other than those which constitute sodium chloride, their osmolarity will be referred to in order to define the osmotic behaviour of the ionic solutions of the invention.

The osmolarity of a solution is designated as the concentration of the osmotically active particles, such as ions, in this solution. In physiology, solutions having an osmolarity equal to that of blood plasma are commonly called <<iso-osmotic>> solutions. Those solutions having a higher osmolarity are called <<hyperosmotic>> solutions.

More specifically, the invention relates to a novel composition in the form of an aqueous solution, notably intended for relieving the sensation of respiratory discomport and/or for promoting the natural regeneration of the mucous membranes of the nasal cavity. This solution is essentially constituted of a levomenthol solution in an aqueous ionic solution having an osmolarity at least equal to that of an aqueous solution of sodium chloride at 9 g/l and in which the levomenthol is dissolved, said aqueous ionic solution being selected from the group constituted of pure or diluted sea water and aqueous sodium chloride solutions optionally further containing at least one salt naturally contained in sea water, the levomenthol being found at a concentration between 10 and 250 mg/l.

This composition has the double advantage of providing:
1) In the first place, an action of washing the nasal mucous membranes congested by a hypertonic or hyperosmotic ionic aqueous solution, or at least an isotonic or iso-osmotic solution. This washing action removes the mucus present on the congested mucous membranes and causes an osmotic effect, and this facilitates the natural regeneration of the mucous membranes of the nasal cavity. This aqueous ionic solution can be either pure or diluted sea water, or it can be water containing sodium chloride and, if need be, other salts naturally contained in sea water. The concentration of sodium chloride, of the solution selected, is preferably equal to or greater than 9 grams per liter, a concentration which is called isotonic with blood or tears.
2) In second place, and additionally, an action on the heat-receptors or cold receptors of the mucous membranes of the nasal cavity. This action is obtained by the use of levomenthol, the only isomer of menthol being active on the heat-receptors or cold receptors, of the mucous membranes of the nasal cavity. Levomenthol acts on the flow of calcium ions through the cell membranes of these receptors. A refreshing effect is thus instantaneously felt and procures a sensation of ease of breathing which enables the sensation of respiratory discomfort due to the nasal congestion to be decreased, in anticipation of a natural regeneration of the mucous membranes of the nasal cavity and without the use of other substances or medicaments which might be dangerous.

DETAILED DESCRIPTION OF THE INVENTION

Hence, the present invention gives a real synergy of the effects of its two constitutive elements, leading to a result which is particularly remarkable by its immediate effect. In fact, the action of the levomenthol is optimised:

(i) by the washing, with an ionic solution, of the mucous membranes of the nasal cavity which has been ridded of mucus, and this renders the heat-receptors more easily accessible to the levomenthol, and (ii) by the absence, in the composition, of combined substances, of the terpene or essential oil type or any other substance, which can decrease the access of the levomenthol to these heat-receptors.

The addition of a substance can be envisaged which is non-active upon the mucous membranes of the nasal cavity for, if need be, stabilising the pH of the composition.

As set forth above, it is important that the composition has an ion content which confers to it an osmotic pressure which is at least equal to that of an isotonic composition of sodium chloride.

On the contrary, too high a concentration of ions would risk leading to a composition which is too irritant for the nasal mucous membranes.

This is the reason why the ionic compositions of the invention advantageously have an osmolarity which is equivalent to that of a solution of sodium chloride between 9 and 30 g/l, preferably between 12 and 18 g/l.

According to a preferred variant of the invention, the ionic solution is pure or diluted sea water having an osmolarity as defined above.

According to another variant, the sea water will be replaced with a solution called <<synthetic sea water>>, which contains sodium chloride and optionally other salts which are naturally contained in natural sea water.

All these solutions, whether it be natural sea water or synthetic sea water, will contain a total content of ions such that they have an osmolarity as defined above.

Copper, zinc, iodine, magnesium, manganese, fluorine, selenium ions, as well as the ions found in trace state in sea water such as nickel, silver or cobalt ions, will be cited as examples amongst the ions introduced in the form of salts in synthetic sea water.

These ions will be introduced for example in one of the following forms:

copper sulphate,
zinc chloride,
potassium iodide,
magnesium sulphate,
manganese chloride,
sodium fluoride,
selenium chloride.

The various ions introduced will preferably be introduced at concentrations which are equal to or less than those usually encountered in sea water, or which are compatible with the standards in force of drinkability of drinking waters, or of acceptability for the composition of mineral waters.

The levomenthol is found in the compositions of the invention at contents at which it is in solution, and this without it being necessary to add products intended for improving its solubility or its dispersability. This constitutes an essential difference with the compositions of the prior art.

To that end, the concentration of the levomenthol in the compositions of the invention is advantageously between 30 and 200 mg/l, preferably between 100 and 180 mg/l.

The two constituents, the aqueous ionic solution and the levomenthol, are called essential constituents of the composition of the present invention in the sense that is is to their presence alone that the activity of the composition is linked. The presence of oil or alcohol, with the view notably to increasing the limit of solubility of the levomenthol in the composition is excluded. Such a presence could further more be harmful.

However, it will be possible to admit the presence of a buffer intended for adjusting the pH to values between 6 and 12, preferably between 8 and 10, in the composition.

Those which are well tolerated by the mucous membranes of the nasal cavity and which can maintain the solution in slightly alkaline medium, e.g. sodium phosphate- or sodium bicarbonate-based buffer solutions, will be cited as examples of acceptable buffer solutions.

An advantage of the compositions of the invention is that, due to their simplicity, they can be prepared very economically, by simple mixing and agitation of their constituents. This mixing can then be followed by a filter in step, optionally by a sterilisation step.

Another advantage of the compositions of the invention is that they do not necessitate the addition of an antiseptic or of an additional preservative; and this further decreases any risk of irritant character.

The classical steps of sterilisation and disinfecting notably by heat means or by irradiation do prove to be entirely sufficient for obtaining perfectly reliable compositions.

The composition of the invention has the advantage of being able to be manufactured industrially in an aseptic and sterile manner, and, without undergoing external microbial contamination which could reveal to be dangerous for the user.

The composition of the present invention is advantageously presented in a suitable device for nasal pulverisation or nebulisation.

As an example, an empty device can be filled with the composition which will beforehand have undergone a sterilising filtration. The device will then be closed or crimped in a way as to affix thereon the valve or the device which will ensure the pulverisation or the nebulisation. The whole of these operations can take place in an aseptic or sterile medium.

It may prove to be useful to pulverise or to nebulise micro-doses of these compositions, so as to repeat these operations several times per day in order to ensure the well-being of the user without risk to health.

According to another of its essential characteristics, the invention relates to the use of a composition in the form of a solution containing from 10 to 250 mg/l of levomenthol in aqueous solution in pure or diluted sea water or in an aqueous solution containing sodium chloride and optionally enriched with at least one ion naturally contained in sea water, said solution having an osmolarity corresponding to that of an aqueous solution of sodium chloride containing from 9 to 30 g/l, preferably 12 to 18 g of sodium chloride, for preparing a composition intended for relieving the sensation of respiratory discomfort and/or for promoting the natural regeneration of the mucous membranes of the nasal cavity.

According to another of its essential characteristics, the invention relates to a method of treatment of colds, according to which the composition as described above is administered by nasal pulverisation or nebulisaton, so as to relieve the sensation of respiratory discomfort and/or to promote the natural regeneration of the mucous membranes of the nasal cavity.

According to another feature, the composition of the invention can be pulverised or nebulised, with the aid of a suitable device, into the external auditory canal, with the view to cleaning this canal and to removing impurities found therein and which, in accumulating, favour the formation of cerumen plugs.

According to another of its essential features, the invention relates to the use of optionally diluted sea water for obtaining an osmolarity which is equivalent to that of a solution of sodium chloride containing from 9 to 30 g/l, and preferably 12 to 18 g/l, or of a solution of sodium chloride optionally farther containing at least one of the salts contained naturally in sea water and having an osmolarity which is equivalent to that of an aqueous solution of sodium chloride containing from 9 to 30 g per liter, preferably from 12 to 18 g of sodium chloride, as an agent intended for improving the sensation of freshness brought about by the levomenthol at the cold receptors of the nasal cavity.

All these compositions described above enable this effect of synergism to be observed between the two essential constituents of the composition and more particularly in the case of concentrations of levomenthol between 10 and 250 mg/l, preferably between 30 and 200 mg/l, more preferably between 100 and 180 g/l.

The Examples which follow are given in a non-limiting way. The compositions which are described therein are obtained by mixing their constituents, filtering sterilising, packing in a nebuliser or pulveriser flask, with or without propellant gas, or by any other method which enables the administration of the composition into the nasal cavity.

EXAMPLE 1

| | |
|---|---|
| levomenthol | 9 mg |
| sea water | 50 ml |

EXAMPLE 2

| | |
|---|---|
| levomenthol | 12 mg |
| purified water | 30 ml |
| sea water | 70 ml |

EXAMPLE 3

| | |
|---|---|
| levomenthol | 1 mg |
| sodium chloride | 135 mg |
| purified water | 15 ml |

EXAMPLE 4

| | |
|---|---|
| levomenthol | 0.5 mg |
| sodium chloride | 350 mg |
| purified water | 15 ml |

EXAMPLE 5

| | |
|---|---|
| levomenthol | 15 mg |
| magnesium sulphate | 5 mg |
| sodium fluoride | 4 mg |
| selenium chloride | 3 mg |
| sodium chloride | 1.2 mg |
| purified water | 100 ml |

EXAMPLE 6

| | |
|---|---|
| levomenthol | 12 mg |
| copper sulphate | 4 mg |
| manganese chloride | 2 mg |
| sodium chloride | 1.4 mg |
| purified water | 100 ml |

EXAMPLE 7

| | |
|---|---|
| levomenthol | 18 mg |
| zinc chloride | 1.5 mg |
| sodium chloride | 1.8 mg |
| purified water | 100 ml |

The compositions described in Examples 1 to 7 are administered in case of colds or in case of a blocked nose, at the rate of 1 to 10 nebulisations of 25 to 150 microliters per day in each nostril.

What is claimed is:

1. A composition for relieving a sensation of respiratory discomfort and/or for promoting natural regeneration of mucous membranes of the nasal cavity, comprising an active ingredient consisting essentially of levomenthol at a concentration between 10 and 250 mg/l, dissolved in an aqueous ionic solution having an osmolarity at least equal to that of an aqueous solution of sodium chloride at 9 g/l, said aqueous ionic solution being selected from the group consisting of pure sea water, diluted sea water, an aqueous sodium chloride solution, an aqueous sodium chloride solution further containing at least one salt found in sea water, and mixtures thereof, said composition further comprising a buffer for adjusting pH which comprises sodium bicarbonate, wherein said composition does not contain an oil or an alcohol.

2. The composition according to claim 1, wherein said ionic solution has an osmolarity which is equivalent to that of an aqueous solution of sodium chloride containing from 9 to 30 g/l of sodium chloride.

3. The composition according to claim 1, wherein said ionic solution has an osmolarity which is equivalent to that of an aqueous solution of sodium chloride containing from 12 to 18 g/l of sodium chloride.

4. The composition according to claim 1, wherein the levomenthol is in solution in pure or diluted sea water having an osmolarity which is equivalent to that of an aqueous solution of sodium chloride containing from 9 to 30 g of sodium chloride per liter.

5. The composition according to claim 4, wherein the osmolarity is equivalent to an aqueous sodium chloride solution containing from 12 to 18 g/l.

6. The composition according to claim 1, wherein the levomenthol is in solution in a solution of sodium chloride containing from 9 to 30 g per liter of sodium chloride.

7. The composition according to claim 6, wherein the levomenthol is in solution in a solution of sodium chloride containing from 12 to 18 g per liter of sodium chloride.

8. The composition according to claim 1, wherein the levomenthol is in solution in an aqueous solution containing sodium chloride, said solution further containing at least one ion selected from the group consisting of copper, zinc, iodine, magnesium, silver, manganese, fluorine, nickel, cobalt and selenium, said solution having an osmolarity which is equivalent to that of a solution of sodium chloride containing from 9 to 30 g/l of sodium chloride.

9. The composition according to claim 8, wherein the osmolarity is equivalent to an aqueous sodium chloride solution containing from 12 to 18 g/l.

10. The composition according to claim 1, containing from 30 to 200 mg/l of levomenthol.

11. The composition according to claim 10, containing from 100 to 180 mg/l of levomenthol.

12. A composition for relieving a sensation of respiratory discomfort and/or for promoting natural regeneration of mucous membranes of the nasal cavity, comprising levomenthol at a concentration between 10 and 250 mg/l, dissolved in an aqueous ionic solution having an osmolarity at least equal to that of an aqueous solution of sodium chloride at 9 g/l, said aqueous ionic solution being selected from the group consisting of pure sea water, diluted sea water, an aqueous sodium chloride solution, an aqueous sodium chloride solution further containing at least one salt found in sea water, and mixtures thereof, wherein said composition contains no oil or alcohol.

13. The composition according to claim 12, wherein said ionic solution has an osmolarity which is equivalent to that of an aqueous solution of sodium chloride containing from 9 to 30 g/l of sodium chloride.

14. The composition according to claim 13, wherein said ionic solution has an osmolarity which is equivalent to that of an aqueous solution of sodium chloride containing from 12 to 18 g/l of sodium chloride.

15. The composition according to claim 12, wherein the levomenthol is in solution in pure or diluted sea water having an osmolarity which is equivalent to that of an aqueous solution of sodium chloride containing from 9 to 30 g of sodium chloride per liter.

16. The composition according to claim 15, wherein the osmolarity is equivalent to an aqueous sodium chloride solution containing from 12 to 18 g/l.

17. The composition according to claim 12, wherein the levomenthol is in solution in a solution of sodium chloride containing from 9 to 30 g per liter of sodium chloride.

18. The composition according to claim 17, wherein the levomenthol is in solution in a solution of sodium chloride containing from 12 to 18 g per liter of sodium chloride.

19. The composition according to claim 12, wherein the levomenthol is in solution in an aqueous solution containing sodium chloride, said solution further containing at least one ion selected from the group consisting of copper, zinc, iodine, magnesium, silver, manganese, fluorine, nickel, cobalt and selenium, said solution having an osmolarity which is equivalent to that of a solution of sodium chloride containing from 9 to 30 g/l of sodium chloride.

20. The composition according to claim 19, wherein the osmolarity is equivalent to an aqueous sodium chloride solution containing from 12 to 18 g/l.

21. The composition according to claim 12, containing from 30 to 200 mg/l of levomenthol.

22. The composition according to claim 21, containing from 100 to 180 mg/l of levomenthol.

23. The composition according to claim 12, further comprising a buffer for adjusting pH.

24. The composition according to claim 23, wherein the buffer comprises sodium bicarbonate.

25. A method of cleaning an external auditory canal for removing impurities found therein, comprising introducing into the external auditory canal an effective amount of a composition comprising levomenthol in a concentration of 10 to 250 mg/l, dissolved in an aqueous solution having an osmolarity corresponding to that of an aqueous solution of sodium chloride containing from 9 to 30 g/l of sodium chloride, said aqueous solution being selected from the group consisting of pure sea water, diluted sea water, an aqueous sodium chloride solution, an aqueous sodium chloride solution further containing at least one salt found in sea water, and mixtures thereof, wherein said composition contains no oil or alcohol.

26. The method according to claim 25, wherein the aqueous solution has an osmolarity corresponding to that of an aqueous solution of sodium chloride containing from 12 to 18 g/l of sodium chloride.

* * * * *